United States Patent [19]

Boschetti et al.

[11] 4,310,536
[45] Jan. 12, 1982

[54] RODENTICIDAL COMPOSITIONS

[75] Inventors: Eugené Boschetti, Venissieux; Jean-Claude Lechevin, Lyons, both of France

[73] Assignee: Lipha, Lyonnaise Industrielle Pharmaceutique, Lyons, France

[21] Appl. No.: 860,468

[22] Filed: Dec. 14, 1977

Related U.S. Application Data

[63] Continuation-in-part of Ser. No. 713,283, Aug. 10, 1976, abandoned.

[30] Foreign Application Priority Data

Aug. 19, 1975 [FR] France ................................ 75 25639
Jul. 13, 1976 [FR] France ................................ 76 21377

[51] Int. Cl.³ .................... A01N 43/16; A01N 35/00
[52] U.S. Cl. .................................... 424/281; 424/331
[58] Field of Search ............................... 424/281, 331

[56] References Cited
U.S. PATENT DOCUMENTS 3,818,100 6/1974 Linhart .............................. 424/281
3,867,546 2/1975 Lechevin .......................... 424/331

OTHER PUBLICATIONS

The Merck Index, Ninth Edition, Published by Merck & Co., Inc., Rahway, N.J., Dec. 27, 1976, 2131 and 3311.

Primary Examiner—Frederick E. Waddell
Attorney, Agent, or Firm—Browdy and Neimark

[57] ABSTRACT

Compositions having rodenticidal activity are disclosed which are constituted by a solution of a compound having anti-coagulant activity and which is an indane dione or a 4-hydroxycoumarin, preferably chlorophacinone, diphacinone, bromadiolone or coumachlor, in a glycol in admixture with a volatile co-solvent, preferably acetone or dichloromethane, which increases the solvent activity of the glycol for the anti-coagulant compound. The composition is stable and may be applied to solid or liquid baits or used to form trail poisons.

5 Claims, No Drawings

RODENTICIDAL COMPOSITIONS

CROSS-REFERENCE TO RELATED APPLICATIONS

The present application is a Continuation-In-Part of U.S. application Ser. No. 713,283, filed Aug. 10, 1976 now abandoned, the entire contents of which are hereby incorporated by reference.

FIELD OF THE INVENTION

This invention relates to compositions having rodenticidal activity and intended for use in the destruction of rodents such as rats and mice, and to a method for the destruction of rodents.

BACKGROUND OF THE INVENTION

Several derivatives of indane-diones and 4-hydroxycoumarins are known to possess the property of lowering the amount of prothrombin in the blood. For this reason, they may be used as rodenticides, producing high mortality in rats and mice by causing internal hemorrhaging. However, compositions containing these compounds lack satisfactory storage properties, tending to be unstable or tending to render bait to which they are applied unattractive to rodents.

U.S. Pat. No. 3,867,546, teaches that certain such rodenticides have an adequate degree of solubility in polyoxyethylene glycols to permit the preparation of solutions which are stable in time. This method, however, cannot be extended to certain other rodenticides of this class or to other glycols because of the problem of limited solubility. In order to obtain the advantages of a stable solution, a sufficient concentration must be achieved.

SUMMARY OF THE INVENTION

Accordingly, it is an object of the present invention to solve these problems of the prior art.

It is another object of the present invention to provide a rodenticidal composition of adequate concentration, which is stable during storage.

It is yet another object of the present invention to provide a rodenticidal composition which does not impair the attraction to rodents of bait to which it is applied.

According to the present invention, there is provided a composition having rodenticidal activity, which comprises an indane-dione or a 4-hydroxycoumarin compound possessing anti-coagulant activity in solution in an admixture of glycol with a volatile co-solvent which improves the solubility of the rodenticide in the glycol.

The present invention also provides a method of killing rodents which comprises applying to or placing in a rodent infested habitat a composition having rodenticidal activity which comprises an indane-dione or a 4-hydroxycoumarin compound possessing anti-coagulant activity in solution in an admixture of glycol and volatile co-solvent.

DETAILED DESCRIPTION OF THE PREFERRED EMBODIMENTS

Certain indane-diones and 4-hydroxycoumarins, particularly chlorophacinone, diphacinone, bromadiolone or coumachlor, exhibit unsatisfactory solubility in glycols, for example propylene glycol, ethylene glycol and polyoxyethylene glycols, such as polyoxyethylene glycol 300, that is, polyoxyethylene glycol of molecular weight 300. Thus, while the solutions are stable over a substantial length of time, the concentrations are not sufficiently high to be of commercial importance.

It has now been found that when the solubility of the rodenticidally active compounds in the glycol is too low for the desired concentration of the compound to be achieved, a volatile co-solvent, miscible with the glycol, for example, dichloromethane or acetone, may be employed to yield a stable solution which may have a greatly improved concentration.

The indane-dione or 4-hydroxycoumarin compounds, the solubility of which are particularly improved by means of the present invention are: 3-α-acetonyl-4-chlorobenzyl)-4-hydroxycoumarin, commonly known as coumachlor, [3-(4'-hydroxy-3'-coumarinyl)-3-phenyl-1-(4'-bromo-4'-biphenyl)]-1-propanol, commonly known as bromadiolone, 1,1-diphenyl-2-acetyl-1,3-indane-dione, commonly known as diphacinone and (1'-p-chlorophenyl-1'-phenyl)-2-acetyl-1,3-indane-dione, commonly known as chlorodiphacinone.

It is important, in order to obtain stable and concentrated rodenticide solutions adapted for storage without deterioration and diminution of concentration, that the dissolution of the rodenticide first take place in the co-solvent. This solution is then mixed with the glycol.

The volatile co-solvent used must be miscible with glycol and a good solvent for the rodenticide. That is, the rodenticide should be substantially more soluble in the co-solvent than in the glycol used.

The weight ratio of glycol to co-solvent must be selected to provide an improved concentration of the rodenticide over that of the rodenticide in the glycol alone. It has been found that an optimum ratio exists for obtaining a maximal concentration without substantially diminishing the storage stability. Above this ratio the solubility will diminish.

For example, it has been shown that the maximum concentration of chlorophacinone in propylene glycol is 0.8 g/kg. This concentration can be increased to 2.5 g/kg by the use of a propylene glycol-acetone mixture at a ratio of 4.5.

The maximum concentration of diphacinone in propylene glycol is also 0.8 g/kg. This concentration can be increased to 2.5 g/kg by use of a solvent mixture of propylene glycol-dichloromethane at a weight ratio of 3.5.

The maximum concentration of bromadiolone in ethylene glycol is 1.25 g/kg. This concentration can be increased to 2.5 g/kg by use of a mixture of ethylene glycol-acetone at a weight ratio of 3.5.

The maximum concentration of coumachlor in ethylene glycol is 5 g/kg. This concentration can be increased to 12.5 g/kg in a mixture of ethylene glycol-acetone at a weight ratio of 12.5 g/kg.

Accordingly, to obtain the optimal increase in concentration, without loss of stability, the weight ratio of glycol to co-solvent should be between about 2.5 and about 5.5. Preferably, for chlorophacinone and coumachlor the ratio should be about 3.5–5.5, most preferably 4.5, and for diphacinone and bromadiolone the ratio should be about 2.5–4.5, most preferably 3.5.

The solutions in the glycol/co-solvent mixture are chemically stable. They can be colored with water-soluble dyes and may contain compounds for imparting an aroma thereto.

These solutions may be used to impregnate baits which are based on cereals, for example wheat, maize, barley and oats, or any other support which is likely to be eaten by the rodents, for example apples or carrots. These solutions can also be used to impregnate an absorbent substance or powder to form a trail poison.

Moreover, when the solutions are diluted with water, they can be used as toxic drinks for the rodents and can be sprayed on plants or parts of plants which are usually eaten by the rodents.

The following Examples illustrate this invention:

EXAMPLE 1

A concentrate of chlorodiphacinone in a mixture of propylene glycol and a volatile co-solvent was prepared by first dissolving 2 g of chlorodiphacinone in 158 g of acetone. After dissolution was complete 840 g of propylene glycol were added. A solution containing 2 g of chlorodiphacinone per kg was obtained.

EXAMPLE 2

A concentrate of coumachlor in a mixture of ethylene glycol and a volatile co-solvent was prepared by first dissolving 10 g of coumachlor in 158 g of acetone. After dissolution was complete 832 g of ethylene glycol were added. A solution containing 10 g of coumachlor per kg was obtained.

EXAMPLE 3

A trail poison containing chlorodiphacinone was prepared by mixing 125 g of the concentrate obtained in Example 1 with 895 g of talc. After drying and evaporating off the acetone, 1 kg of a trail poison containing 0.25 g of chlorodiphacinone per kg was obtained.

It will be obvious to those skilled in the art that various changes may be made without departing from the scope of the invention and the invention is not to be considered limited to what is described in the specification.

What is claimed is:

1. A composition having rodenticidal activity comprising a compound selected from the group consisting of chlorophacinone, diphacinone, bromadiolone, and coumachlor, in a rodenticidal amount, dissolved at substantially the maximum stable concentration thereof, in a glycol selected from the group consisting of ethylene glycol and propylene glycol, and a volatile co-solvent, miscible with said glycol, in which said compound is more soluble than in said glycol, said glycol and said co-solvent being in a weight ratio selected to provide a greater solubility of said compound than in said glycol alone under otherwise identical conditions, said weight ratio being within the range of about 2.5–5.5.

2. A composition in accordance with claim 1, wherein said volatile co-solvent is acetone or dichloromethane.

3. A composition in accordance with claim 2, wherein said compound is chlorophacinone or coumachlor and the weight ratio of said glycol to said co-solvent is about 3.5–5.5.

4. A composition in accordance with claim 2, wherein said compound is diphacinone or bromadiolone and the weight ratio of said glycol to said co-solvent is about 2.5–4.5.

5. A composition in accordance with claim 1, wherein said composition is the product of the process in which said compound is first dissolved in said volatile co-solvent and then the solution is mixed with said glycol.

* * * * *